(12) United States Patent
Pennington

(10) Patent No.: US 7,010,182 B2
(45) Date of Patent: Mar. 7, 2006

(54) BIOSENSORS HAVING ENHANCED ENVIRONMENTAL SENSITIVITY

(75) Inventor: Charles D. Pennington, Blacksburg, VA (US)

(73) Assignee: Luna Innovations Incorporated, Blacksburg, VA (US)

( * ) Notice: Subject to any disclaimer, the term of this patent is extended or adjusted under 35 U.S.C. 154(b) by 243 days.

(21) Appl. No.: 10/417,976

(22) Filed: Apr. 17, 2003

(65) Prior Publication Data

US 2004/0022475 A1    Feb. 5, 2004

Related U.S. Application Data

(60) Provisional application No. 60/399,937, filed on Jul. 31, 2002.

(51) Int. Cl.
    *G02B 6/00*    (2006.01)
(52) U.S. Cl. .................. 385/12; 385/39; 385/123
(58) Field of Classification Search ................ 385/12, 385/123
    See application file for complete search history.

(56) References Cited

U.S. PATENT DOCUMENTS

| | | | |
|---|---|---|---|
| 4,842,783 A * | 6/1989 | Blaylock ................. | 264/1.27 |
| 4,846,548 A | 7/1989 | Klainer | |
| 5,052,820 A | 10/1991 | McGinniss et al. | |
| 5,864,641 A * | 1/1999 | Murphy et al. .............. | 385/37 |
| 5,900,215 A | 5/1999 | Seifert et al. | |
| 5,982,959 A | 11/1999 | Hopenfeld | |
| 6,035,082 A * | 3/2000 | Murphy et al. .............. | 385/37 |
| 2001/0040679 A1 | 11/2001 | Kawabata et al. | |
| 2002/0128234 A1 * | 9/2002 | Hubbell et al. ............. | 514/100 |
| 2003/0152345 A1 * | 8/2003 | Viswanathan et al. ...... | 385/123 |

OTHER PUBLICATIONS

Petar R. Dvornic, Agnes De Leuze-Jallouli, Michael J. Owne, and Susan V. Perez, "Nanostructured Films, Coatings, molecular "Sponges" and "Reactors" from Copolymeric Amidoamine-Organosilicon (PAMAMOS) Dendrimers," Polymer Preprints, 1999, vol. 40, pp. 408-409.

* cited by examiner

*Primary Examiner*—Brian Healy
*Assistant Examiner*—Eric Wong
(74) *Attorney, Agent, or Firm*—Joy L. Bryant

(57) ABSTRACT

A biosensor having enhanced sensitivity to physical or chemical parameters comprises a waveguide and a coating disposed on the waveguide. The coating has a refractive index that enhances the sensitivity of the biosensor to physical or chemical parameters. In a preferred embodiment, the coating comprises at least one dendrimer disposed on the waveguide, wherein the coating has a refractive index ranging from about 1.0 to about 1.5. A method for fabrication of the biosensor is also provided.

13 Claims, 6 Drawing Sheets

BIOSENSORS HAVING ENHANCED ENVIRONMENTAL SENSITIVITY

CROSS-REFERENCE TO RELATED APPLICATIONS

This application claims the benefit of U.S. Provisional Application No. 60/399,937, entitled "Biosensors Having High Refractive Indices," filed Jul. 31, 2002, hereby incorporated by reference in its entirety.

FIELD OF THE INVENTION

The present invention relates to biosensors having enhanced sensitivities to physical or chemical parameters. In particular, it relates to biosensors having a dendrimer coating.

BACKGROUND OF THE INVENTION

When sensors are employed in the detection of biological materials in a particular environment, it is sometimes necessary to be able to detect refractive index changes within a certain range. Therefore, it is desirable to be able to tailor the fabrication of the optical sensor to be sensitive to a specific refractive index range. This has been accomplished in the past by applying coatings to the surface of the optical sensor. In particular, Murphy et al. (U.S. Pat. No. 5,864,641) disclose an optical fiber long period grating sensor having a reactive coating positioned in an operable relationship to the long period grating wherein the reactive coating causes the long period grating to produce a wavelength transmission spectrum functionally dependent on a sensed parameter. They describe the coating as being either physically reactive, electrically reactive, or chemically reactive. More specifically, the chemically reactive coating is described as one which undergoes a chemical change when exposed to certain target materials. The reaction may either change the chemical or physical composition of the coating. For example, when the chemically reactive coating has target sites present, a chemical bond is formed between the target site and a specific molecule. In this instance, there is a change in the wavelength transmission spectrum produced by the long period grating which results from exposure of the reactive coating to certain substances. They describe the coating as a concentrated solution of a material having active sites, such as antibodies, which are deposited directly on the waveguide so the active sites attach directly to the waveguide. Alternatively, the coating may be a complex formulation having other materials compounded along with the material with the active sites such that the active sites are attached within the coating. Specifically, these active sites are described as low molecular weight ligands. When the coating is deposited on the waveguide, the active sites are oriented away from the waveguide so they are able to complex with specific target molecules. The coating may also be compounded to have the active sites undergo a change in the physical property of the coating when in comes in contact with a specific material. In this instance, the coating may be solvated by a specific solvent, thus causing the thickness of the coating to change which ultimately changes the coating's refractive index profile. Lastly, the coating is described as one which may have active sites which bond with fluorescent dyes. In all instances, the reactive coating is described as one capable of producing a wavelength transmission spectrum functionally dependent on a specific parameter which is sensed. However, the coatings described by Murphy et al. are deficient for applications requiring high sensitivity within a specific refractive index range.

An object of the present invention is to provide a biosensor that has a coating having a refractive index that is tailored to enhance the sensitivity of the biosensor to an environmental parameter.

Another object of the invention is to provide a biosensor that has a coating having a refractive index ranging from about 1.0 to about 1.5.

Another object of the present invention is to provide a biosensor that has a coating which permits enhanced sensitivity, an operational wavelength that may be tailored to the application, and has increased binding capacity.

Another object of the present invention is to provide a method of fabrication of a biosensor which has a coating having a refractive index ranging from about 1.0 to about 1.5.

SUMMARY OF THE INVENTION

The present invention is a biosensor comprising a waveguide and a coating disposed on the waveguide. The coating has a refractive index that effects the sensitivity of the biosensor to a physical or chemical parameter. In a preferred embodiment, the coating comprises at least one dendrimer and has a refractive index ranging from about 1.0 to about 1.5. The dendrimers have a weight average molecular weight ranging from about 200 to about 60,000.

Additional objects and advantages of the invention will be set forth in part in the description which follows, and in part will be obvious from the description, or may be learned by practice of the invention. The objects and advantages of the invention will be obtained by means of instrumentalities in combinations particularly pointed out in the appended claims.

BRIEF DESCRIPTION OF THE DRAWINGS

The accompanying drawings illustrate a complete embodiment of the invention according to the best modes so far devised for the practical application of the principles thereof, and in which.

DETAILED DESCRIPTION OF THE PREFERRED EMBODIMENTS

The present invention is directed towards applications for biosensors where enhanced sensitivity to a physcial or chemical parameter is desired. The biosensor comprises a waveguide and a coating, having a refractive index, disposed on the waveguide. The refractive index of the coating enhances the sensitivity of the biosensor to a physical or chemical parameter. Any coating known to those of skill in the art having a refractive index in the desired range may be suitable as the coating for the present invention. Preferably, such coatings contain dendrimers.

Dendrimer polymers and dendrimers contain a central core, an interior dendritic structure, and an exterior surface (the end groups). Dendrimers differ from linear polymeric compounds because the dendrimer has an ordered structure and can be highly branched with known molecular weights and functional end groups. These compounds are classified as nanomaterials. Presently, 50 compositionally different families of dendrimers exist, with over 200 end group modifications. The size of the dendrimer is controlled by the growth cycle during the synthesis of the material and is referred to as the generation number. For example, a polyamidoamine dendrimer is available as generation −0.5 (molecular weight 436.28 with 4 carboxylate end groups) through generation 4.5 (molecular weight 26,258 with 128 carboxylate end groups). These materials are commercially available from Aldrich Chemical Company.

Figure 1:
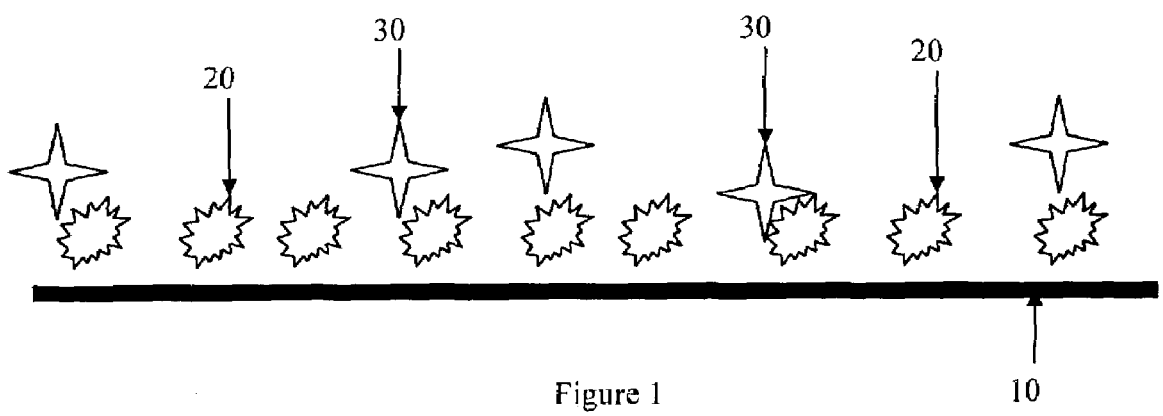
FIG. 1 is a schematic representation of a preferred embodiment of the invention showing a dendrimer coating attached to a waveguide surface and how a binding receptor attaches to the dendrimer coating.

In the present invention, it was discovered that the sensitivity of a biosensor was greatly enhanced when a coating comprising at least one dendrimer was disposed on a waveguide. For biological applications, it is desirable to have the refractive index of the coating ranging from about 1.0 to about 1.5. FIG. 1 is a schematic drawing depicting a preferred embodiment of the present invention. The waveguide surface 10 is coated with a coating 20 comprising at least one dendrimer. When the biosensor is exposed to certain targeted binding receptors 30, a bond is formed between the dendrimer and the binding receptor causing a change in the refractive index which is due to the bound mass captured. Because the dendrimer is a nanomaterial, it is possible to, although not limited to, apply it as a monolayer with increased sensitivity to the binding receptor, thus overcoming the problems associated with thicker coating layers such as those of Murphy et al.

Figure 2:
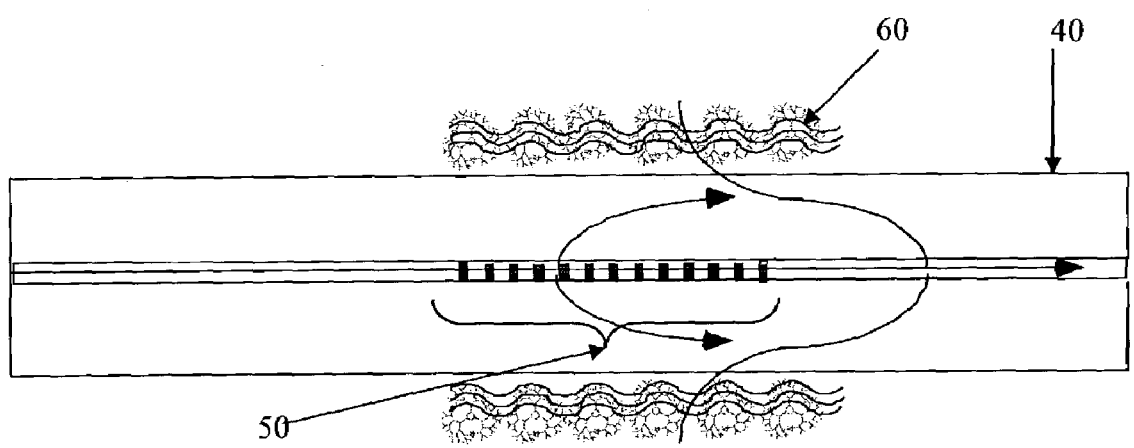
FIG. 2 depicts an optical fiber having a long period grating disposed therein and a dedrimer coating disposed thereon.

Any waveguide known to those of ordinary skill in the art may be employed for the present invention. For example, surface plasmon resonance, fiber optic waveguides, fiber optic waveguides having Bragg gratings disposed therein, fiber optic waveguides having long period gratings disposed therein, planar optic waveguides, and evanescent waveguides may be used. By evanescent waveguides it is meant that the evanescent field has been extended out of the waveguide into the surrounding environment. Fiber optic waveguides are preferred. More specifically, fiber optic waveguides having long period gratings disposed therein were found to be most suitable for the biosensor application. FIG. 2 depicts a fiber optic waveguide 40 having a long period grating 50 disposed therein. A coating comprising a dendrimer 60 is disposed on the fiber optic waveguide 40 in an operable relationship to the long period grating 50.

Figure 3:
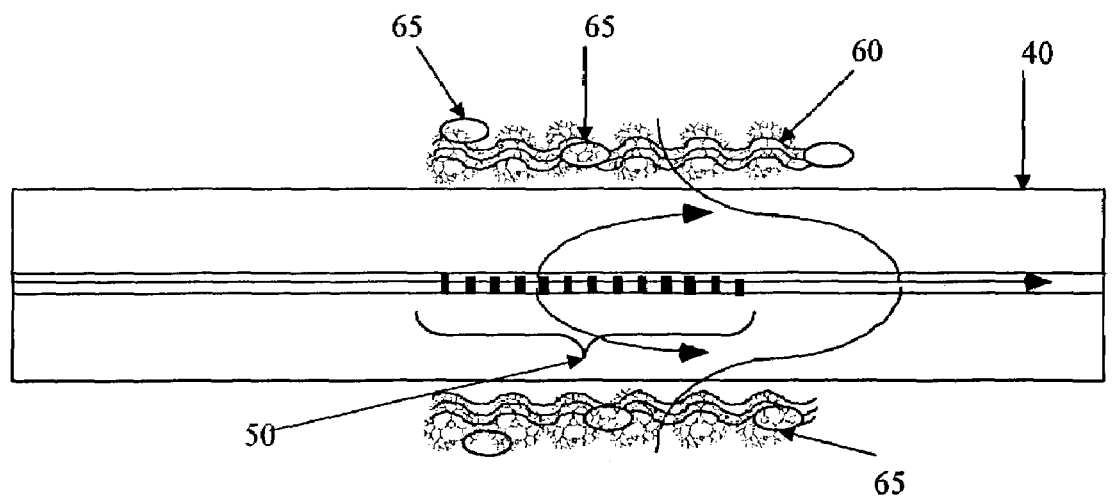
FIG. 3 depicts an optical fiber having a long period grating disposed therein and a dendrimer coating having a protein attached to it disposed thereon.

FIG. 3 depicts another embodiment of the invention wherein the dendrimer coating 60 has a protein 65 attached to it. In this embodiment, the fiber optic waveguide 40 has a long period grating 50 disposed therein. The dendrimer coating 60 having a protein 65 attached to it, is disposed on the fiber optic waveguide 40 in an operable relationship to the long period grating.

Figure 4:
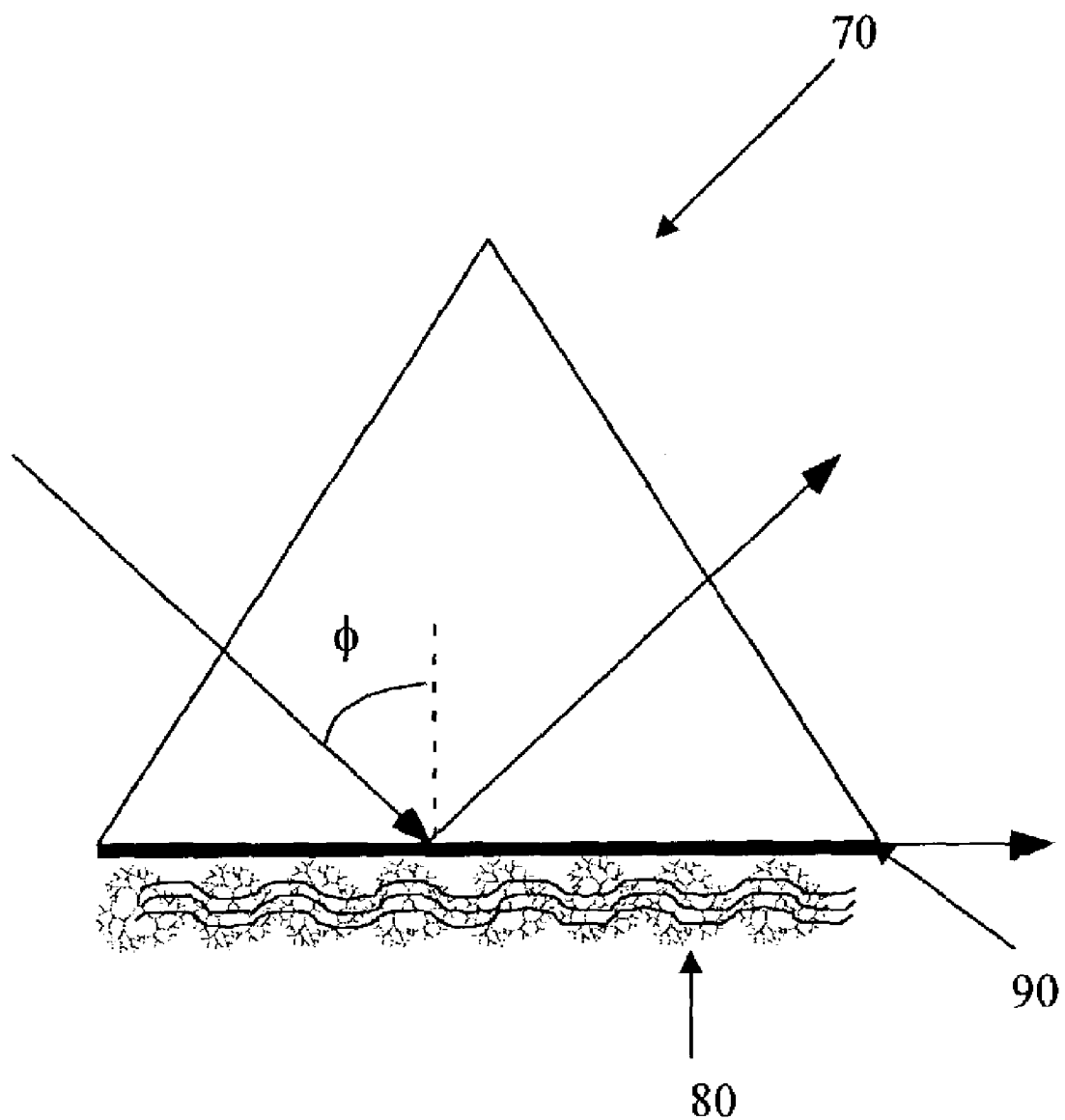
FIG. 4 depicts a surface plasmon resonance arrangement having a dendrimer coating.

FIG. 4 depicts a surface plasmon resonance (SPR) arrangement 70 where a dendrimer 80 coating is disposed on a metallic surface 90. In this arrangement, the gold surface 90 of the SPR sensor has been modified using either a self-assembled monolayer reagent containing an active thiol group, such as an alkane thiol, or a homobifunctional reagent that contains a disufide bridge and terminal active groups. The thiol reagent contains a second functional group which is used to couple proteins, receptors, DNA, or other material to the modified SPR surface. Examples of these thiol reagents include but are not limited to a hydroxyl, carboxylic acid, or amine group. The homobifunctional reagents adsorb onto the gold surface through a disulfide group such that the terminal group will allow further covalent immobilization of amino-containing organic molecules. One example of a homobifunctional reagent is Dithiobis(N-succinimidyl propionate) (DTSP), also known as Lomant's reagent.

Figure 5:
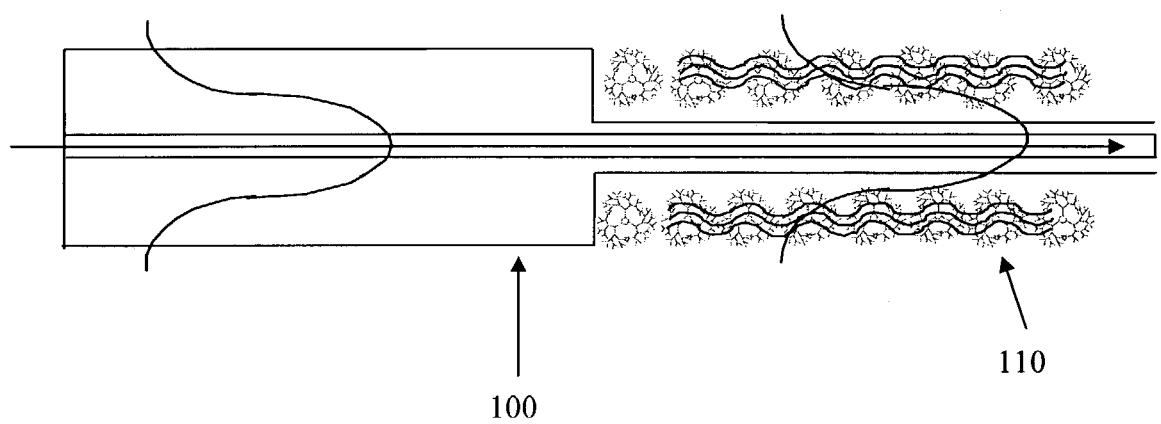
FIG. 5 depicts an evanescent waveguide sensor having a dendrimer coating disposed thereon.

FIG. 5 depicts another type of optical waveguide, an evanescent waveguide 100. As in the fiber optic waveguide, a coating comprising a dendrimer 110 is disposed on the evanescent waveguide 100 in an operable relationship to the core of the waveguide.

The dendrimers used in the present invention are all commercially available from Aldrich Chemical Company. Any dendrimer known to those of skill in the art is suitable for the present application. In particular, dendrimers having functional endgroups selected from the group consisting of: primary amine; carboxylate; hydroxyl; and sulfhydryl have been found to be suitable for biological applications. The dendrimers may be of any weight average molecular weight ranging from about 200 to about 60,000. Preferably, the weight average molecular weight ranges from about 400 to about 30,000 and most preferably, the weight average molecular weight is about 436. Alternatively, the weight average molecular weight is about 6267. It was found that the molecular weight of the dendrimer effects the refractive index of the coating and thus, the ultimate sensitivity of the sensor to certain environments is affected. Preferably the dendrimers found suitable for biological applications were selected from the group consisting of: a polyamidoamine dendrimer with primary amino surface groups; a polypropyleneimine dendrimer with primary amino surface groups; a polyamidoamine dendrimer with hydroxyl surface groups; and a polyamidoamine dendrimer with carboxylate surface groups. Most preferably, the dendrimer is a polyamidoamine dendrimer with carboxylate surface groups. The coating may comprise only one type of dendrimer or a combination of dendrimers. When a combination of dendrimers is employed, the functional endgroups of the dendrimers may be different.

In a preferred embodiment of the invention, the biosensor comprises a fiber optic waveguide having a long period grating disposed therein. The dendrimer coating comprises a polyamidoamine dendrimer with carboxylate surface groups having a weight average molecular weight of about 436 and a refractive index of about 1.38. The dendrimer coating is disposed on the fiber optic waveguide in an operable relationship to the long period grating.

The fabrication technique for an optical biosensor includes the steps of providing an optical waveguide having a glass surface. Any optical waveguide having a glass surface, known to those of skill in the art, may be used such as a fiber optic waveguide, a fiber optic waveguide having a Bragg grating disposed therein, a fiber optic waveguide having a long period grating disposed therein, or an evanescent waveguide. Preferably the optical waveguide is a fiber optic waveguide having a long period grating disposed therein or an evanescent waveguide. The optical waveguide is cleaned to remove debris. Any known method for cleaning optical waveguides may be used such as applying hydrogen peroxide, sodium hydroxide, or an alcohol/hyrdochloric acid mixture to the waveguide. The optical waveguide is then rinsed. After rinsing, the optical waveguide is exposed to a functionalized silane mixture. Examples of a functionalized silane mixture include but are not limited to a primary aminosilane mixture or a carboxysilane mixture. The functionality of the silane mixture is determined by the endgroups on the dendrimers. For example, if the dendrimers have a carboxyl endgroup, then an aminosilane mixture would be used. After applying the functionalized silane mixture, the optical waveguide is rinsed and the dendrimer solution is applied. The dendrimer solution comprises a dendrimer with a suitable crosslinking agent, 1-ethyl-3-(3-dimethylaminopropyl)carbodiimide (EDAC), and a buffer solution wherein the buffer solution has a pH ranging from about 5 to about 7. More specifically, the buffer solution comprises 4-morpholine ethanesulfonic acid and the pH is about 6.8. The optical waveguide is exposed to the dendrimer solution at room temperature for about one hour to form a dendrimer coating on the optical waveguide. The dendrimer coated optical waveguide is then rinsed with a buffer solution and the resulting dendrimer coated optical waveguide is stored in the buffer solution until the time of use. Alternatively, dendrimer layers can be applied to the fiber surface to further enhance the refractive index of the coating (ultimately effecting sensitivity to an environmental parameter) and control the coating thickness using multiple layers. The dendrimer coated optical biosensors prepared from this method are found to have refractive index sensitivities ranging from about 1.0 to about 1.5.

The dendrimer coated optical biosensors may be further reacted with a protein to form a protein coated dendrimer coated optical biosensor. These types of sensors are fabricated by activating the glass surface of the dendrimer coated optical waveguide. This is achieved by exposing the dendrimer coated optical waveguide for about one hour to a mixture of 1-ethyl-3-(3-dimethylaminopropyl)carbodiimide, N-hydroxy-succinimide, and a buffer solution having a pH ranging from about 5 to about 7. The activated dendrimer coated optical waveguide is then washed with a buffer solution. The activated dendrimer coated optical waveguide is then exposed to a protein solution in an acetate buffered solution having a pH ranging from about 4 to about 6 for about one hour. The protein solution comprises from about 1 µg/ml to about 5 mg/ml of protein to form a protein coated dendrimer coated optical waveguide. Preferably, the protein solution contains about 100 µg/ml of protein. The protein coated dendrimer coated optical waveguide is rinsed with the acetate buffer solution having a pH ranging from about 4 to about 6 and then exposed for about one hour in an endcapping solution having a pH ranging from about 8.5 to about 10. In particular, the endcapping solution comprises an endcapper selected from the group consisting of ethanolamine; carboxyl; and sulfhydryl. The protein coated dendrimer coated optical waveguide is rinsed and stored in a phosphate buffer saline solution having a pH ranging from about 6.5 to about 8.

Alternatively, another preparation method for surface plasmon resonance biosensors is by exposing a sensor having a gold surface to a 10 mM solution of dithiobis(N-succinimidyl propionate) in dimethyl sulfoxide (DMSO) for 30 minutes. The surface is then rinsed with DMSO followed by rinsing with water. The sensor is then exposed to an amino-containing material (such as a protein at a concentration of about 1.0 to about 6.0 mg/mL in a 0.1 M phosphate buffer having a pH of about 7.0) for about 1.5 hours. The sensor is then rinsed with a 0.1 M phosphate buffer solution having a pH of about 7.0.

EXAMPLES

Example 1

A Protein A coated sensor was prepared by providing a glass fiber having a long period grating disposed therein. The glass fiber was cleaned with a solution of methanol and hydrochloric acid in a 1:1 mixture for 1 hour at room temperature. The fiber was rinsed with methanol. The fiber was soaked in a 10% solution of 3-aminopropyl-trimethoxysilane in methanol for 1 hour at room temperature. The fiber was then rinsed with methanol. Next, the fiber was soaked in a solution of 1 mM Polyamidoamine dendrimer (G −0.5) (available from Aldrich Chemical Company) and 19 mg/ml of 1-ethyl-3-(3-dimethylaminopropyl)carbodiimide (EDAC) and 20 mM Morpholineethanesulfonic acid (MES) (available from Sigma) at a pH of 6.8 for 1 hour at room temperature. The fiber was rinsed with a 20 mM MES pH 6.8 buffer solution. Next the fiber was soaked in a 20 mM MES pH 6.8 buffer solution containing 19 mg/ml of 1-ethyl-3-(3-dimethylaminopropyl)carbodiimide (EDAC) and 7.5 mg/ml N-hydroxysuccinimide for 1 hour at room temperature. The fiber was then rinsed with 10 mM sodium acetate pH 5.0 buffer solution. The fiber was soaked in a 10 mM sodium acetate pH 5.0 buffer solution containing 0.1 mg/mL of Protein A (available from Sigma) for 1 hour at room temperature. The fiber was rinsed with 10 mM sodium acetate pH 5.0 buffer solution. The fiber was soaked in a 1 M ethanolamine pH 9.0 solution for 1 hour at room temperature. The fiber was rinsed with phosphate buffered saline pH 7.2 and stored in the same buffer at 2–8 degrees Celsius.

Example 2

Figure 6:
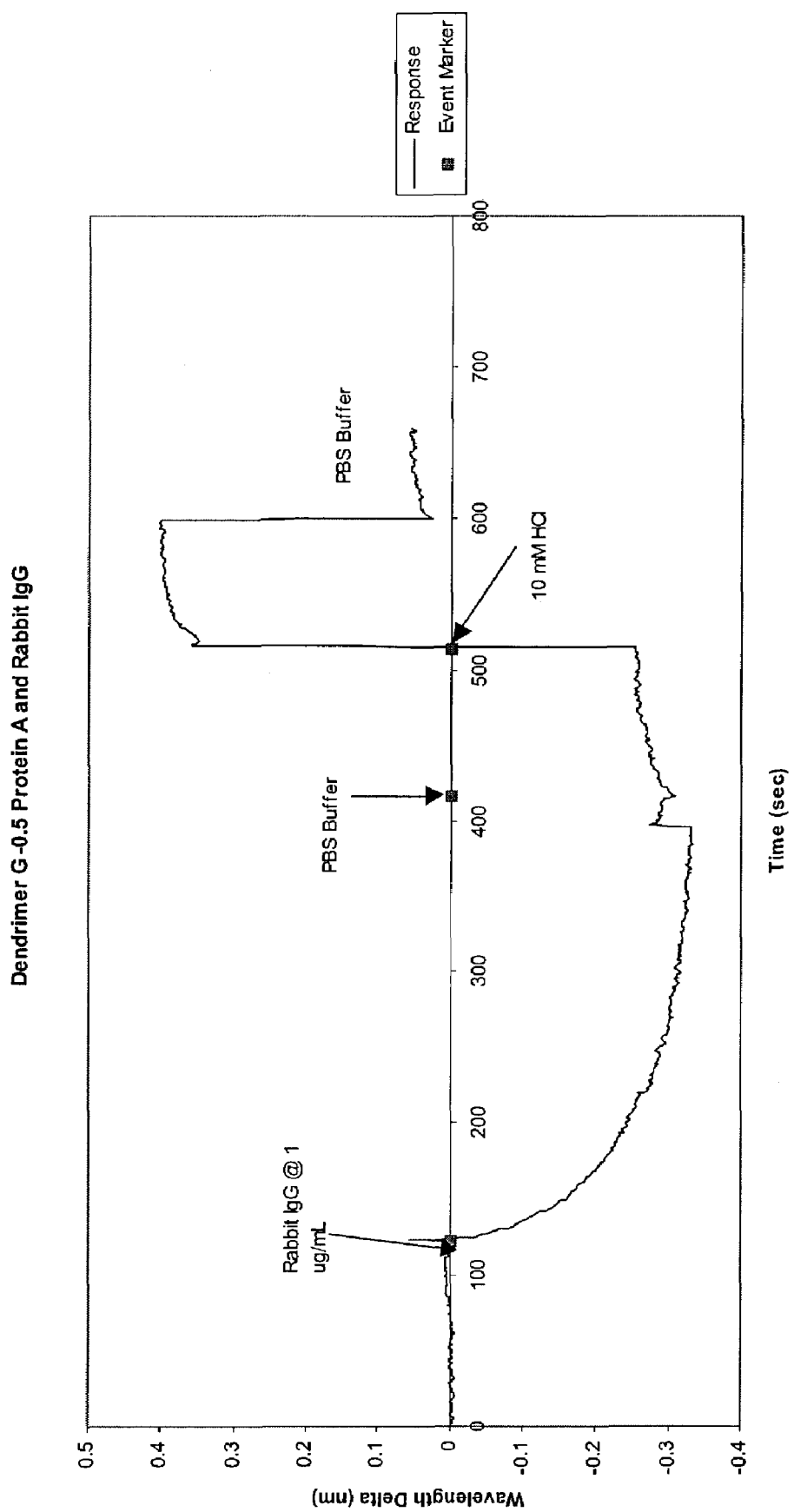
FIG. 6 is a graph depicting how rabbit IgG binds to a dendrimer coating comprising protein A which has been disposed on an optical fiber.

The Protein A coated sensor of example 1 was used to monitor the response of the sensor to rabbit IgG. The Protein A coated sensor was exposed to a phosphate buffered saline pH 7.2 (PBS) to establish a baseline signal for the sensor. (See FIG. 6) The sensor was then exposed to a 1 µg/mL solution of rabbit immunoglobulin (IgG, Technical grade available from Sigma) in PBS pH 7.2. As shown in FIG. 6, the rabbit IgG had bound to the protein A on the surface of the fiber sensor. To remove any unbound material from the sensor surface, the fiber was exposed to PBS pH 7.2 buffer. Next, the fiber was exposed to 10 mM Hcl to remove the bound IgG material from the protein A and to regenerate the fiber for a subsequent assay cycle. Lastly, the fiber was exposed to a PBS pH 7.2 buffer solution to re-establish a baseline and return the sensor to a buffered environment.

The above description and drawings are only illustrative of preferred embodiments which achieve the objects, features and advantages of the present invention, and it is not intended that the present invention be limited thereto. Any modification of the present invention which comes within the spirit and scope of the following claims is considered part of the present invention.

What is claimed is:
1. A biosensor, comprising:
a waveguide; and
a coating, having refractive index ranging from about 1.0 to about 1.5, wherein the coating comprises at least one dendrimer disposed on the waveguide and wherein the refractive index of the coating enhances sensitivity of the biosensor.

2. A biosensor according to claim 1, wherein each dendrimer has functional endgroups selected from the group consisting of: primary amine; carboxylate; hydroxyl; and sulfhydryl.

3. A biosensor according to claim 2 wherein the coating comprises at least two dendrimers and wherein the functional endgroups of each dendrimer are different.

4. A biosensor according to claim 2, wherein the coating comprises at least two dendrimers and wherein the functional endgroups of each dendrimer are the same.

5. A biosensor according to claim 1, wherein each dendrimer has a weight average molecular weight ranging from about 200 to about 60,000.

6. A biosensor according to claim 5, wherein each dendrimer has a weight average molecular weight ranging from about 400 to about 30,000.

7. A biosensor according to claim 6, wherein each dendrimer has a weight average molecular weight of about 436.

8. A biosensor according to claim 6, wherein each dendrimer has a weight average molecular weight of about 6267.

9. A biosensor according to claim 1, wherein each dendrimer is selected from the group consisting of: a polyamidoamine dendrimer with primary amino surface groups; a polypropyleneimine dendrimer with primary amino surface groups; a polyamidoamine dendrimer with hydroxyl surface groups; and a polyamdioamine dendrimer with carboxylate surface groups.

10. A biosensor according to claim 9, wherein the dendrimer is a polyamidoamine dendrimer with carboxylate surface groups.

11. A biosensor according to claim 1, wherein the waveguide is selected from the group consisting of: surface plasmon resonance waveguide; a fiber optic waveguide; a fiber optic waveguide having a Bragg grating disposed therein; a fiber optic waveguide having a long period grating disposed therein; and an evanescent waveguide.

12. A biosensor according to claim 11, wherein the waveguide is a fiber optic waveguide having a long period grating disposed therein.

13. A biosensor comprising a fiber optic waveguide having a long period grating disposed therein; and a coating having a refractive index of about 1.38 wherein the coating comprises a polyamidoamine dendrimer with carboxylate surface groups having a weight average molecular weight of about 436, wherein the coating is disposed on the fiber optic waveguide.

* * * * *